United States Patent
Duggan

(10) Patent No.: US 9,238,054 B2
(45) Date of Patent: Jan. 19, 2016

(54) TREATMENT OF KIDNEY FIBROSIS WITH VIP FRAGMENTS

(71) Applicant: Vectus Biosystems Pty Limited, Rosebery, NSW (AU)

(72) Inventor: Karen Annette Duggan, Randwick (AU)

(73) Assignee: VECTUS BIOSYSTEMS PTY LIMITED, Roseberry, New South Wales (AU)

(*) Notice: Subject to any disclaimer, the term of this patent is extended or adjusted under 35 U.S.C. 154(b) by 71 days.

(21) Appl. No.: 14/034,706

(22) Filed: Sep. 24, 2013

(65) Prior Publication Data

US 2014/0080758 A1 Mar. 20, 2014

Related U.S. Application Data

(62) Division of application No. 13/124,139, filed as application No. PCT/AU2009/001367 on Oct. 16, 2009, now Pat. No. 8,569,235.

(30) Foreign Application Priority Data

Oct. 17, 2008 (AU) ............................... 2008905378

(51) Int. Cl.
- *A61K 38/22* (2006.01)
- *A61P 13/12* (2006.01)
- *C07K 14/575* (2006.01)
- *A61K 38/10* (2006.01)
- *A61K 38/08* (2006.01)
- *A61K 38/00* (2006.01)

(52) U.S. Cl.
CPC ................. *A61K 38/10* (2013.01); *A61K 38/08* (2013.01); *A61K 38/2278* (2013.01); *C07K 14/57563* (2013.01); *A61K 38/00* (2013.01)

(58) Field of Classification Search
None
See application file for complete search history.

(56) References Cited

U.S. PATENT DOCUMENTS

| 7,951,777 | B2 * | 5/2011 | Duggan | 514/13.1 |
| 8,470,778 | B2 * | 6/2013 | Duggan | 514/13.1 |
| 8,569,235 | B2 * | 10/2013 | Duggan | 514/13.1 |
| 8,916,523 | B2 * | 12/2014 | Duggan | 514/13.1 |

FOREIGN PATENT DOCUMENTS

| WO | 03/105765 | 12/2003 |
| WO | 2004/048401 | 6/2004 |
| WO | 2006/012394 | 2/2006 |
| WO | 2007/065226 | 6/2007 |

OTHER PUBLICATIONS

Arnaout, M.A., et al., Prolactin responses to vasoactive intestinal polypeptide and thyrotropin releasing hormone in chronic renal failure, Acta Endocrinologica (Copenh), 1991, vol. 125, No. 6, pp. 651-656.

(Continued)

*Primary Examiner* — Zachary Howard
(74) *Attorney, Agent, or Firm* — Wenderoth, Lind & Ponack, L.L.P.

(57) ABSTRACT

The invention relates to compositions comprising vasoactive intestinal peptide (VIP) or fragments thereof, and the use of such compositions in the treatment of kidney disease, in particular kidney fibrosis, and other associated conditions.

8 Claims, 4 Drawing Sheets

(56) References Cited

OTHER PUBLICATIONS

Meyer, M., et al., Basic aspects of vasorelaxant and bronchodilating peptides in clinical use: Urodilatin, VIP and PACAP, Annals New-York Academy of Sciences, 1996, vol. 805, pp. 443-461.
International Search Report for PCT/AU2009/001367 dated Jan. 4, 2010.
Lekgabe et al (2005) Hypertension 46:412-418.
Wells (1990) Biochemistry 29(37): 8509-8517.
Ngo et al (1994) The Protein Folding Problem and Tertiary Structure Prediction, Chapter 14: Computational Complexity Protein Structure Prediction, and the Levinthal Paradox, pp. 433-440 and 492-495 only.
Bork (2000) Genome Research 10:398.
Skolnick et al (2000) Trends in Biotech. 18(1):34.
Doerks et al (1998) Trends in Genetics 14(6):248.
Brenner (1999) Trends in Genetics 15(4):132.
Wada et al (2007) Kidney International 72: 269-273.

* cited by examiner

* p<0.005, p<0.001, *p<0.0005 vs Control

SEQUENCE LISTING

<160> NUMBER OF SEQ ID NOS: 11

<210> SEQ ID NO 1
<211> LENGTH: 28
<212> TYPE: PRT
<213> ORGANISM: Homo sapiens

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 19
<212> TYPE: PRT
<213> ORGANISM: Homo sapiens

<400> SEQUENCE: 2

Tyr Thr Arg Leu Arg Lys Gln Met Ala Val Lys Lys Tyr Leu Asn Ser
1               5                   10                  15

Ile Leu Asn

<210> SEQ ID NO 3
<211> LENGTH: 9
<212> TYPE: PRT
<213> ORGANISM: Homo sapiens

<400> SEQUENCE: 3

Ala Val Phe Thr Asp Asn Tyr Thr Arg
1               5

<210> SEQ ID NO 4
<211> LENGTH: 13
<212> TYPE: PRT
<213> ORGANISM: Homo sapiens

<400> SEQUENCE: 4

Ala Val Phe Thr Asp Asn Tyr Thr Arg Leu Arg Lys Gln
1               5                   10

<210> SEQ ID NO 5
<211> LENGTH: 17
<212> TYPE: PRT
<213> ORGANISM: Homo sapiens

<400> SEQUENCE: 5

Ala Val Phe Thr Asp Asn Tyr Thr Arg Leu Arg Lys Gln Met Ala Val
1               5                   10                  15

Lys

<210> SEQ ID NO 6
<211> LENGTH: 21
<212> TYPE: PRT
<213> ORGANISM: Homo sapiens

<400> SEQUENCE: 6

Ala Val Phe Thr Asp Asn Tyr Thr Arg Leu Arg Lys Gln Met Ala Val
1               5                   10                  15

Lys Lys Tyr Leu Asn
            20

```
<210> SEQ ID NO 7
<211> LENGTH: 5
<212> TYPE: PRT
<213> ORGANISM: Homo sapiens

<400> SEQUENCE: 7

Phe Thr Asp Asn Tyr
1               5

<210> SEQ ID NO 8
<211> LENGTH: 7
<212> TYPE: PRT
<213> ORGANISM: Homo sapiens

<400> SEQUENCE: 8

Phe Thr Asp Asn Tyr Thr Arg
1               5

<210> SEQ ID NO 9
<211> LENGTH: 11
<212> TYPE: PRT
<213> ORGANISM: Homo sapiens

<400> SEQUENCE: 9

Phe Thr Asp Asn Tyr Thr Arg Leu Arg Lys Gln
1               5                   10

<210> SEQ ID NO 10
<211> LENGTH: 15
<212> TYPE: PRT
<213> ORGANISM: Homo sapiens

<400> SEQUENCE: 10

Phe Thr Asp Asn Tyr Thr Arg Leu Arg Lys Gln Met Ala Val Lys
1               5                   10                  15

<210> SEQ ID NO 11
<211> LENGTH: 19
<212> TYPE: PRT
<213> ORGANISM: Homo sapiens

<400> SEQUENCE: 11

Phe Thr Asp Asn Tyr Thr Arg Leu Arg Lys Gln Met Ala Val Lys Lys
1               5                   10                  15

Tyr Leu Asn
```

TREATMENT OF KIDNEY FIBROSIS WITH VIP FRAGMENTS

TECHNICAL FIELD

This invention relates to compositions and methods for therapeutic or prophylactic treatment of chronic kidney disease. In particular this invention concerns compositions comprising VIP or certain active fragments of VIP and their use in the treatment of chronic kidney disease, kidney fibrosis or kidney failure.

BACKGROUND

Any discussion of the prior art throughout the specification should in no way be considered as an admission that such prior art is widely known or forms part of common general knowledge in the field.

Chronic kidney disease (CKD) affects approximately 10% of the general population in the western world. Data from the UK and the US indicate that while the incidence of CKD is approximately 2% of the young adult population, it rises markedly with age reaching an incidence of 50% in the population aged over 75 years. These figures will increase as a consequence of the ageing of western populations and secondly from the increase in Type II diabetes flowing from the obesity epidemic. Most patients with Type II diabetes have evidence of renal damage, such as microalbuminuria, at the time of the diagnosis of their diabetes, and so an increase in the incidence of diabetes will automatically increase the incidence of early stage CKD. It will probably also increase the incidence of later stage CKD. A little over a decade ago diabetes ranked $3^{th}$ or $4^{th}$ as a cause for entry into renal replacement therapy programmes (dialysis and/or transplantation). While other causes have remained static or have increased only slightly, diabetes has increased to being the most common reason for entry into end stage renal failure programmes in less than a decade.

In CKD the progressive loss of renal function occurs as a consequence of the deposition of fibrous tissue between the functional units of the kidney or nephrons (interstitial fibrosis) as well as the ongoing replacement of the filtration surface by fibrous tissue (glomerular sclerosis). Some studies indicate that the former (interstitial fibrosis) may be more important than the latter (glomerular sclerosis) in determining whether a patient progresses to end stage. While primary glomerular damage is also important in the development of CKD and end stage renal disease (ESRD) there is evidence that increased interstitial fibrosis accelerates the loss of glomerular function by causing ischaemic damage to glomeruli— through collapsing the tufts and thickened capsules leading to obsolescence. Through this mechanism, interstitial fibrosis accelerates the progression of renal disease to end stage. Currently available treatments (such as ACE inhibitors, angiotensin receptor blockers, rennin inhibitors) alter glomerular haemodynamics reducing intraglomerular pressure thereby acting to stabilise glomerular sclerosis. In general they slow but do not prevent the progression of CKD. With an increasing prevalence of CKD clearly there is a substantial need to reduce the need for renal replacement therapy by preventing and/or reversing renal fibrosis.

VIP was discovered by Said and Mutt in the 1970's and has been shown to affect urinary sodium and bicarbonate excretion by the kidney. Systemic VIP administration also increases renin secretion by the kidney, which may be profibrotic as renin has recently been shown to have pro-inflammatory and pro-fibrotic properties. Acute VIP administration decreases glomerular filtration rate and renal plasma flow but the effects of chronic administration are not known. VIP administered prior to the insult has been shown to protect against acute renal failure, which occurs due to haemorrhage. However, the mechanisms involved in hypovolaemic acute renal failure (low perfusion pressure and hypoxia) are not contributory to the progression of CKD. Agents which lower blood pressure have been shown to slow the progression of chronic kidney disease by reducing intraglomerular pressure and thus decreasing the progression of glomerular sclerosis. VIP is a potent vasodilator, however unaided VIP does not lower blood pressure in the whole animal.

Conventional view of structure/function relationship with respect to VIP activity is that the N-terminal amino acid residues (1-5) are important and necessary for signal delivery once VIP binds to its receptor. Further, there are certain key amino acid residues throughout the VIP molecule, distal to the N-terminus, that are important for receptor binding. This would suggest that fragments of VIP lacking either the N-terminal residues or significant portions that encompass the receptor binding residues would not be fully functional.

Activity of VIP or fragments of VIP in the treatment of conditions such as kidney fibrosis, chronic kidney disease or kidney failure, has not been previously reported. Need currently exists for better and/or alternative treatments for such conditions.

It is therefore an object of the present invention to overcome or ameliorate at least one of the disadvantages of the prior art, or to provide a useful alternative.

SUMMARY OF THE INVENTION

The present invention is based in part on the observation that VIP and/or VIP fragments have the ability to prevent the development, or reverse established fibrosis in the kidney. Despite the currently prevailing view, the activity of VIP and its fragments in the treatment and/or prevention of chronic kidney disease and fibrosis is not curtailed by either deletion of the N-terminal residues of VIP or the majority of amino acid residues responsible for receptor binding.

According to a first aspect, the invention provides a composition for the prophylactic or therapeutic treatment of chronic kidney disease, the composition comprising a pharmaceutically effective amount of vasoactive intestinal peptide (VIP) or one or more functional VIP fragments selected from VIP(10-28), VIP(4-12), VIP(4-16), VIP(4-20), VIP(4-24), VIP(6-10), VIP(6-12), VIP(6-16), VIP(6-20), VIP(6-24) or conservative substitutions thereof. Preferably, the associated condition is kidney fibrosis.

According to a second aspect, the invention provides a composition for the prophylactic or therapeutic treatment of kidney failure, the composition comprising a pharmaceutically effective amount of vasoactive intestinal peptide (VIP) or one or more functional VIP fragments selected from VIP (10-28), VIP(4-12), VIP(4-16), VIP(4-20), VIP(4-24), VIP(6-10), VIP(6-12), VIP(6-16), VIP(6-20), VIP(6-24) or conservative substitutions thereof.

According to a third aspect, the invention provides a composition for the prophylactic or therapeutic treatment of kidney fibrosis, the composition comprising a pharmaceutically effective amount of vasoactive intestinal peptide (VIP) or one or more functional VIP fragments selected from VIP(10-28), VIP(4-12), VIP(4-16), VIP(4-20), VIP(4-24), VIP(6-10), VIP(6-12), VIP(6-16), VIP(6-20), VIP(6-24) or conservative substitutions thereof.

Preferably, the compositions according to the present invention are administered in conjunction with a pharmaceutically acceptable carrier, which may be any of those known in the art or devised hereafter and suitable for the intended use. As well as carriers, the pharmaceutical composition of the invention may include other ingredients, including dyes, preservatives, buffers and anti-oxidants, for example. They may preferably be administered in conjunction with one or more other active agents useful in the treatment of kidney conditions. They may, for preference, be formulated for administration by oral, intravenous, intramuscular or subcuticular routes. Other methods of administration such as patches, snuffs, nasal sprays and the like, will be clear to those skilled in the art.

The pharmaceutically effective amount of VIP or an active VIP fragment will vary according to the patient's general condition and/or the exact nature and severity of the disease. These variables can be ascertained by one skilled in the art based on experience and with routine experimentation only. An appropriate dosage range, as a starting point, can be derived from dosages administered in the animal models described herein, or with reference to PCT/AU2005/000835. The compositions of the invention may be used to prevent or slow down progression of established kidney disease or condition, particularly fibrosis, as well as to reduce the degree of, or prevent establishment of fibrosis.

According to a fourth aspect, the invention provides a method of prophylactic or therapeutic treatment of chronic kidney disease in a subject, the method comprising administering to the subject at risk of developing chronic kidney disease, or to a subject having chronic kidney disease, a composition comprising a pharmaceutically effective amount of vasoactive intestinal peptide (VIP) or one or more functional VIP fragments selected from VIP(10-28), VIP(4-12), VIP(4-16), VIP(4-20), VIP(4-24), VIP(6-10), VIP(6-12), VIP(6-16), VIP(6-20), VIP(6-24) or conservative substitutions thereof.

With respect to prophylactic treatment it will be understood that such a treatment would benefit particularly subjects who are at risk of developing chronic kidney disease and/or kidney fibrosis. As an example of subjects in the risk category are those having associated conditions such as hypertension, diabetes, glomerulonephritis, heavy metal poisoning, gout, drugs such as cis-platinum and others which are used in cancer chemotherapy, as well as gold and penicillamine which are used in treatment of rheumatoid arthritis, genetic predisposition, other conditions such as reflux nephritis, SLE and vasculitis, and the like.

The prophylactic treatment may be used to prevent or slow down the development of fibrosis in a subject having fibrosis or at risk of developing fibrosis.

According to a fifth aspect, the invention provides a method of prophylactic or therapeutic treatment of kidney failure in a subject, the method comprising administering to the subject at risk of developing kidney failure, or to a subject having kidney failure a composition comprising a pharmaceutically effective amount of vasoactive intestinal peptide (VIP) or one or more functional VIP fragments selected from VIP(10-28), VIP(4-12), VIP(4-16), VIP(4-20), VIP(4-24), VIP(6-10), VIP(6-12), VIP(6-16), VIP(6-20), VIP(6-24) or conservative substitutions thereof.

According to a sixth aspect, the invention provides a method of prophylactic or therapeutic treatment of kidney fibrosis in a subject, the method comprising administering to the subject at risk of developing kidney fibrosis, or to a subject having kidney fibrosis, a composition comprising a pharmaceutically effective amount of vasoactive intestinal peptide (VIP) or one or more functional VIP fragments selected from VIP(10-28), VIP(4-12), VIP(4-16), VIP(4-20), VIP(4-24), VIP(6-10), VIP(6-12), VIP(6-16), VIP(6-20), VIP(6-24) or conservative substitutions thereof.

The prophylactic treatment may be used effectively to prevent or slow down the progression of established chronic kidney disease, in particular established fibrosis, in a subject or it may be used to prevent the development of fibrosis in a subject at risk of developing fibrosis.

Conditions that are associated with, or predispose a subject to, the development of kidney fibrosis include those which give rise to generation of profibrotic mediators.

It will be apparent to one skilled in the art that the pattern of use of the compositions of the invention and the dosage regimen may need to be altered for optimum effect. It may be necessary to take into account the nature of the disease or condition as well as its severity.

According to a seventh aspect, the invention provides vasoactive intestinal peptide (VIP) or one or more functional VIP fragments selected from VIP(10-28), VIP(4-12), VIP(4-16), VIP(4-20), VIP(4-24), VIP(6-10), VIP(6-12), VIP(6-16), VIP(6-20), VIP(6-24) or conservative substitutions thereof, for use in the prophylactic or therapeutic treatment of chronic kidney disease.

According to an eighth aspect, the invention provides vasoactive intestinal peptide (VIP) or one or more functional VIP fragments selected from VIP(10-28), VIP(4-12), VIP(4-16), VIP(4-20), VIP(4-24), VIP(6-10), VIP(6-12), VIP(6-16), VIP(6-20), VIP(6-24) or conservative substitutions thereof, for use in the prophylactic or therapeutic treatment of kidney failure.

According to a ninth aspect, the invention provides vasoactive intestinal peptide (VIP) or one or more functional VIP fragments selected from VIP(10-28), VIP(4-12), VIP(4-16), VIP(4-20), VIP(4-24), VIP(6-10), VIP(6-12), VIP(6-16), VIP(6-20), VIP(6-24) or conservative substitutions thereof, for use in the therapeutic or prophylactic treatment of kidney fibrosis.

Preferably, the use is to prevent or slow down progression of established chronic kidney disease. Alternatively, the use is to prevent or slow down the development of fibrosis in a subject at risk of developing fibrosis. The use is also for reducing the degree of established fibrosis.

According to a tenth aspect, the invention provides a method of reducing the levels, inhibiting or reducing the production of pro-fibrotic mediators in a subject at risk of developing, or having kidney disease, the method comprising administering to the subject a composition comprising a pharmaceutically effective amount of vasoactive intestinal peptide (VIP) or one or more functional VIP fragments selected from VIP(10-28), VIP(4-12), VIP(4-16), VIP(4-20), VIP(4-24), VIP(6-10), VIP(6-12), VIP(6-16), VIP(6-20), VIP(6-24) or conservative substitutions thereof.

According to an eleventh aspect, the invention provides a method of reducing collagen formation or enhancing collagen degradation in the kidney of a subject, the method comprising administering to the subject a composition comprising a pharmaceutically effective amount of vasoactive intestinal peptide (VIP) or one or more functional VIP fragments selected from VIP(10-28), VIP(4-12), VIP(4-16), VIP(4-20), VIP(4-24), VIP(6-10), VIP(6-12), VIP(6-16), VIP(6-20), VIP(6-24) or conservative substitutions thereof.

In the context of the present invention certain terms may be used interchangeably or incorporated within a term with a broader meaning. Thus, the term "kidney disorder" or "kidney disease" may be used interchangeably. The term "chronic kidney disease" "kidney disease" may encompass conditions such as kidney fibrosis and kidney failure. The term "associated condition" as used in the context of the present invention is intended to encompass conditions and disorders that arise as a direct consequence of kidney disease as well as conditions that predispose to development or exacerbation of kidney disease. For example, the term "associated condition" in reference to kidney disease may encompass, without limitation, glomerulonephritis, tubulo-interstitial disease, reflux nephropathy, polycystic disease, SLE, vasculitis, scleroderma, Sjogrens Syndrome, gout, hypertension, diabetes and kidney fibrosis.

The term "prophylactic" as used in the context of the present invention is intended inter alia to encompass treatments used to prevent or slow down the development of fibrosis in the at risk subject. A proportion of subjects that may be given prophylactic treatment may already have signs of kidney disease.

In the context of the present invention the term "therapeutic" is intended to mean partially or completely curative treatment of an existing condition.

It will be understood that the present invention also encompasses within its scope certain analogues of the VIP fragments, which are based on conservative substitutions of one or more amino acids of the VIP fragments, with amino acids which do not alter the biological activities of the VIP fragments. Such substitutions would be well known to those skilled in the art and would not require more than simple trial-and-error using well-established techniques. Hence, the term "VIP fragment" as used in the context of the present invention is intended to encompass such analogues.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

DESCRIPTION OF THE PREFERRED EMBODIMENT

Figure 1:
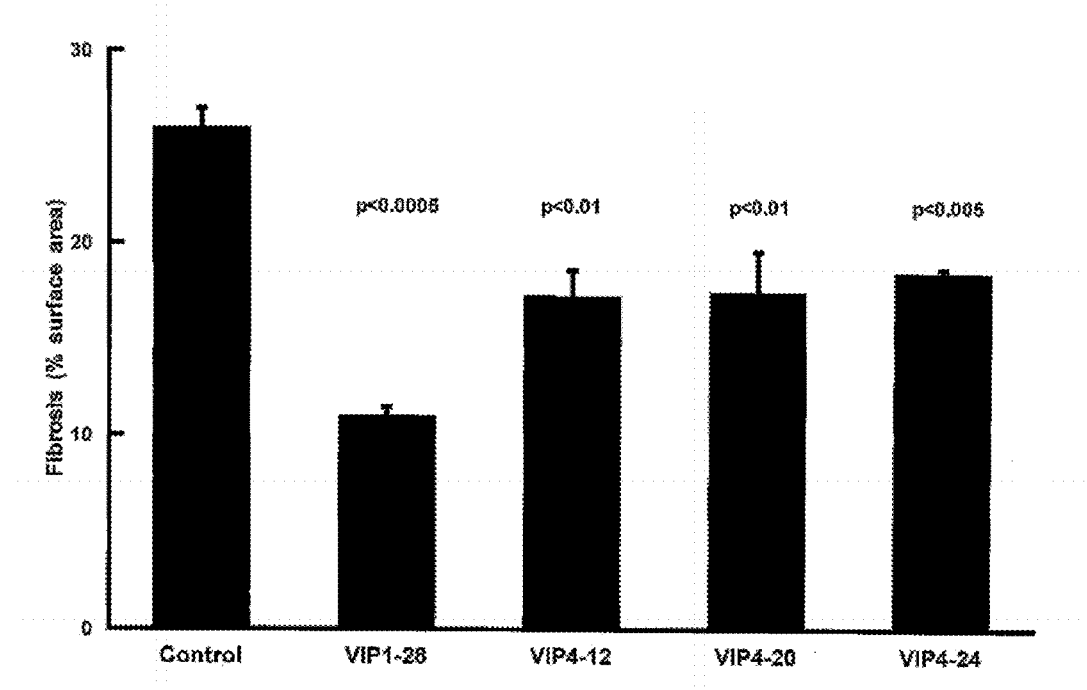
FIG. 1: Renal interstitial fibrosis after infusion of vehicle control or peptide at 5 pmol/kg/min for 4 weeks in the SHR on 2.2% salt diet.

Surprisingly it has now been found that the VIP molecule as a whole, acts to prevent, reduce or reverse kidney fibrosis and thus prevent or slow the progression of chronic kidney disease. Further, in view of the well accepted views held in this field, it has surprisingly been found that VIP fragments lacking amino acids and motifs thought to be important for their function are nevertheless useful therapeutic agents to reverse or delay onset of kidney fibrosis, or prevent onset of fibrosis in subjects at risk of developing kidney disease. Particularly useful VIP fragments can be selected from, but not limited to, VIP(10-28), VIP(4-12), VIP(4-16), VIP(4-20), VIP(4-24), VIP(6-10), VIP(6-12), VIP(6-16), VIP(6-20), VIP(6-24). VIP or VIP fragments are also useful in the treatment of kidney failure.

The use of the pharmaceutical compositions of the invention in the treatment of chronic kidney disease or associated conditions represents a new class of therapeutic agents for these conditions. Existing treatments for chronic kidney disease or associated conditions usually target one, or at the most two, of the known causative mechanisms in chronic kidney disease. Without wishing to be bound by any particular mechanism of action, it is believed that the compositions or pharmaceutical preparations of the present invention may target virtually all the currently known promoters of kidney disease.

On the basis of the present studies, and not wishing to be bound by theory, it is postulated that VIP or VIP fragments act as major regulators to prevent the development of fibrosis, and that the depletion of VIP may unleash the synthesis of a number of profibrotic mediators, thereby causing kidney injury. The VIP fragments of the present invention seem to be able to act in much the same way as the native VIP but are more suited for therapeutic applications due to smaller size and hence increased stability and ease of manufacture.

All the sequences relate to VIP and fragments of human origin, but due to the very high level of amino acid conservation, VIP and fragments thereof derived from other mammalian species are also contemplated and encompassed by the present invention.

The present invention also contemplates pharmaceutical compositions, which include VIP and/or active VIP fragments. Such compositions may include any type of dosage form such as tablets, capsules, powders, liquid formulations, delayed or sustained release, patches, snuffs, nasal sprays and the like. The formulations may additionally include other ingredients such as dyes, preservatives, buffers and anti-oxidants, for example. The physical form and content of the pharmaceutical formulations contemplated are conventional preparations that can be formulated by those skilled in the pharmaceutical formulation field and are based on well established principles and compositions described in, for example, The Science and Practice of Pharmacy, $19^{th}$ Edition, 1995 (Mack Publishing Co. Pennsylvania, USA); British Pharmacopoeia 2000, and similar formulation texts and manuals. The compositions of the present invention may also include other active agents useful in the treatment of kidney disease, kidney failure or kidney fibrosis.

The route and frequency of administration of the compositions of the present invention will depend on the treatment requirements and the nature of the molecule to be administered. Thus the formulations may be suitably prepared for administration by intravenous, intramuscular or subcuticular injection. VIP and/or VIP fragments may also be suitable for mucosal administration such as oral, sublingual, nasal and the like. These parameters are easily established by those skilled in the art.

The pharmaceutical compositions of the invention have been shown to be effective in preventing or slowing down progression of established kidney fibrosis, as well as in reducing the degree (reversal) of established fibrosis and thus important in therapeutic applications. The compositions of the present invention are also useful for prophylactic or therapeutic treatment of chronic kidney disease. These are important findings with respect to the range and severity of conditions, which can be treated with the compositions of the present invention.

Further, the compositions of the present invention may be used prophylactically in subjects at risk of developing chronic kidney disease or an associated condition. As an example of subjects in the risk category are those having associated conditions such as hypertension, diabetes, glomerulonephritis, heavy metal poisoning, gout, drugs such as cis-platinum and others which are used in cancer chemotherapy, as well as gold and pencillamine which are used in treatment of rheumatoid arthritis, genetic predisposition, other conditions such as reflux nephritis, SLE and vasculitis and the like.

By conserving the VIP content of the kidney in a subject with, or at risk of developing, chronic kidney disease or an associated condition, through the use of the compositions of the present invention, significant therapeutic benefits can be achieved. The benefits include reduction of fibrosis, reduction in the level, production or activity of pro-fibrotic mediators, reduction in progression of fibrosis, reduction in collagen formation or enhancing collagen degradation in the kidney.

The invention will now be described more particularly with reference to non-limiting examples.

EXPERIMENTAL

All general methodology and techniques have been described in detail in PCT/AU2005/000835, which is incorporated in its entirety herein by reference.

Example 1

Amino Acid Sequence of VIP and VIP Fragments

All VIP fragments were obtained from or synthesised by Auspep, Australia.

```
                                                 (SEQ ID NO: 1)
VIP(1-28)-His-Ser-Asp-Ala-Val-Phe-Thr-Asp-Asn-
Tyr-Thr-Arg-Leu-Arg-Lys-Gln-Met-Ala-Val-Lys-Lys-
Tyr-Leu-Asn-Ser-Ile-Leu-Asn (SEQ ID NO: 2)
VIP(10-28)-Tyr-Thr-Arg-Leu-Arg-Lys-Gln-Met-Ala-
Val-Lys-Lys-Tyr-Leu-Asn-Ser-Ile-Leu-Asn (SEQ ID NO: 3)
VIP(4-12)-Ala-Val-Phe-Thr-Asp-Asn-Tyr-Thr-Arg (SEQ ID NO: 4)
VIP(4-16)-Ala-Val-Phe-Thr-Asp-Asn-Tyr-Thr-Arg-
Leu-Arg-Lys-Gln (SEQ ID NO: 5)
VIP(4-20)-Ala-Val-Phe-Thr-Asp-Asn-Tyr-Thr-Arg-
Leu-Arg-Lys-Gln-Met-Ala-Val-Lys (SEQ ID NO: 6)
VIP(4-24)-Ala-Val-Phe-Thr-Asp-Asn-Tyr-Thr-Arg-
Leu-Arg-Lys-Gln-Met-Ala-Val-Lys-Lys-Tyr-Leu-Asn (SEQ ID NO: 7)
VIP(6-10)-Phe-Thr-Asp-Asn-Tyr (SEQ ID NO: 8)
VIP(6-12)-Phe-Thr-Asp-Asn-Tyr-Thr-Arg (SEQ ID NO: 9)
VIP(6-16)-Phe-Thr-Asp-Asn-Tyr-Thr-Arg-Leu-Arg-
Lys-Gln (SEQ ID NO: 10)
VIP(6-20)-Phe-Thr-Asp-Asn-Tyr-Thr-Arg-Leu-Arg-
Lys-Gln-Met-Ala-Val-Lys (SEQ ID NO: 11)
VIP(6-24)-Phe-Thr-Asp-Asn-Tyr-Thr-Arg-Leu-Arg-
Lys-Gln-Met-Ala-Val-Lys-Lys-Tyr-Leu-Asn
```

Example 2

Effect of VIP Fragment Infusion on Kidney Fibrosis in Rat Models of Fibrosis

For kidney fibrosis experiments, two types of rats were used, spontaneously hypertensive rats (SHR) and normotensive control Wistar-Kyoto rats (WKY) (animals were obtained from Australian Animal Resources, Perth, Western Australia, Australia)

i) Male spontaneously hypertensive (SHR) rats on 2.2% salt diet ii) Male Wistar Kyoto (WKY) rats on 4.4% salt diets In each model the rats were randomised to VIP(1-28), VIP(10-28), VIP(4-12), VIP(4-16), VIP(4-20), VIP(4-24), VIP(6-10), VIP(6-12), VIP(6-16), VIP(6-20), VIP(6-24).

Commencing at 12 weeks of age, the rats were acclimatized to tail cuff blood pressure measurements and handling for 2 weeks. They then underwent operative insertion of an osmotic minipump (Alzet—Manufacturer: Durect Corporation, Cupertino, Calif., USA; Supplier: Bioscientific Gymea, NSW, Australia) which was designed to deliver vehicle alone (Hartman's solution, Baxter Health Care Corporation, USA)—(Controls) or VIP, VIP fragment or analogue at a dose of 4 pmol/kg/min or 5 pmol/kg/min intravenously.

The infusion was continued for 4 weeks, during which the rats were weighed and their blood pressures measured twice weekly. At the end of the 4 week infusion period, the rats were anaesthetized and their kidneys harvested.

After fixation in buffered formalin the kidneys were embedded in wax, sectioned and stained with haematoxylin and eosin or with Masson Trichrome (Lomb Scientific, USA).

For quantitation of interstitial fibrosis, twenty microscopic fields from each kidney were digitized and the amount of fibrosis in each determined as percent surface area using Image-Pro Plus V5.0 software (Cybernetics). The mean value for each rat and subsequently for each infusion group was then determined.

Figure 2:
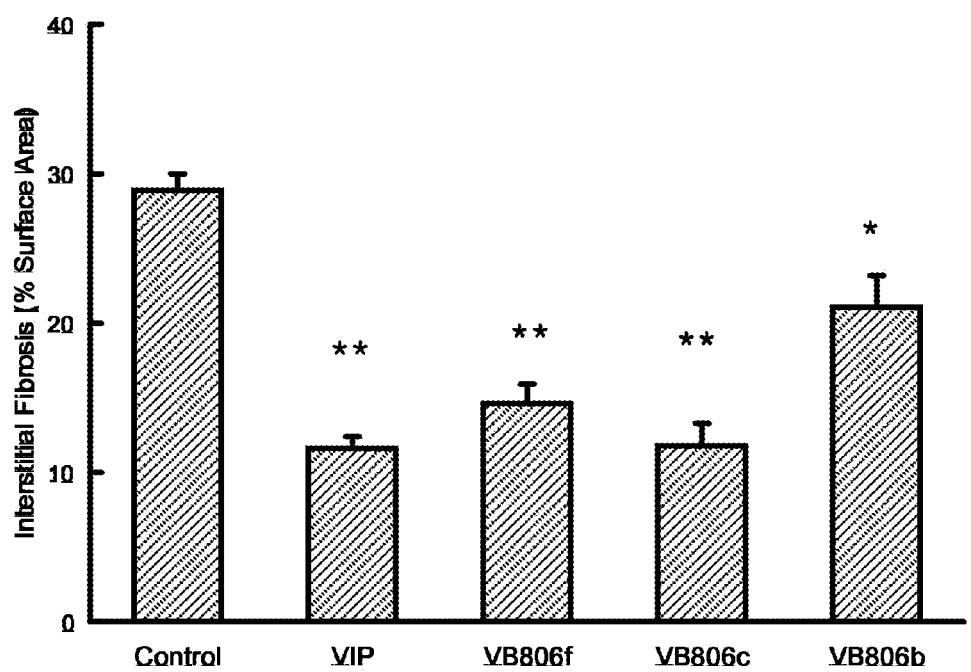
FIG. 2: Renal interstitial fibrosis after infusion of vehicle control or peptide at 5 pmol/kg/min for 4 weeks in the SHR on a 2.2% diet. VB806f refers to VIP(6-10), VB806c refers to VIP(6-20), VB806b refers to VIP(6-24).
Figure 3:
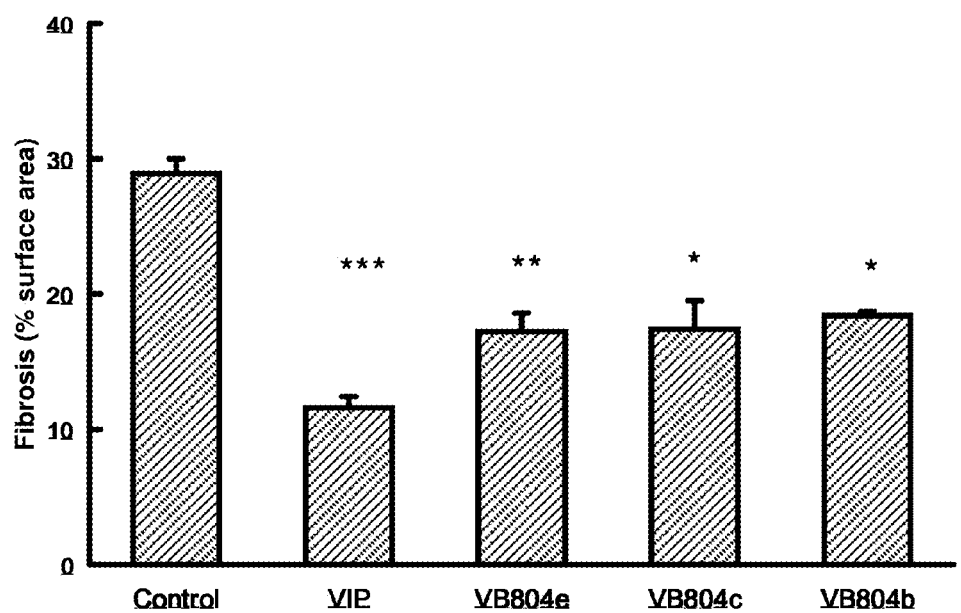
FIG. 3: Renal interstitial fibrosis after infusion of vehicle control or peptide at 5 pmol/kg/min for 4 weeks in SHR on a 2.2% salt diet. VB804e refers to VIP(4-12), VB804c refers to VIP(4-20), VB804b refers to VIP(4-24).
Figure 4:
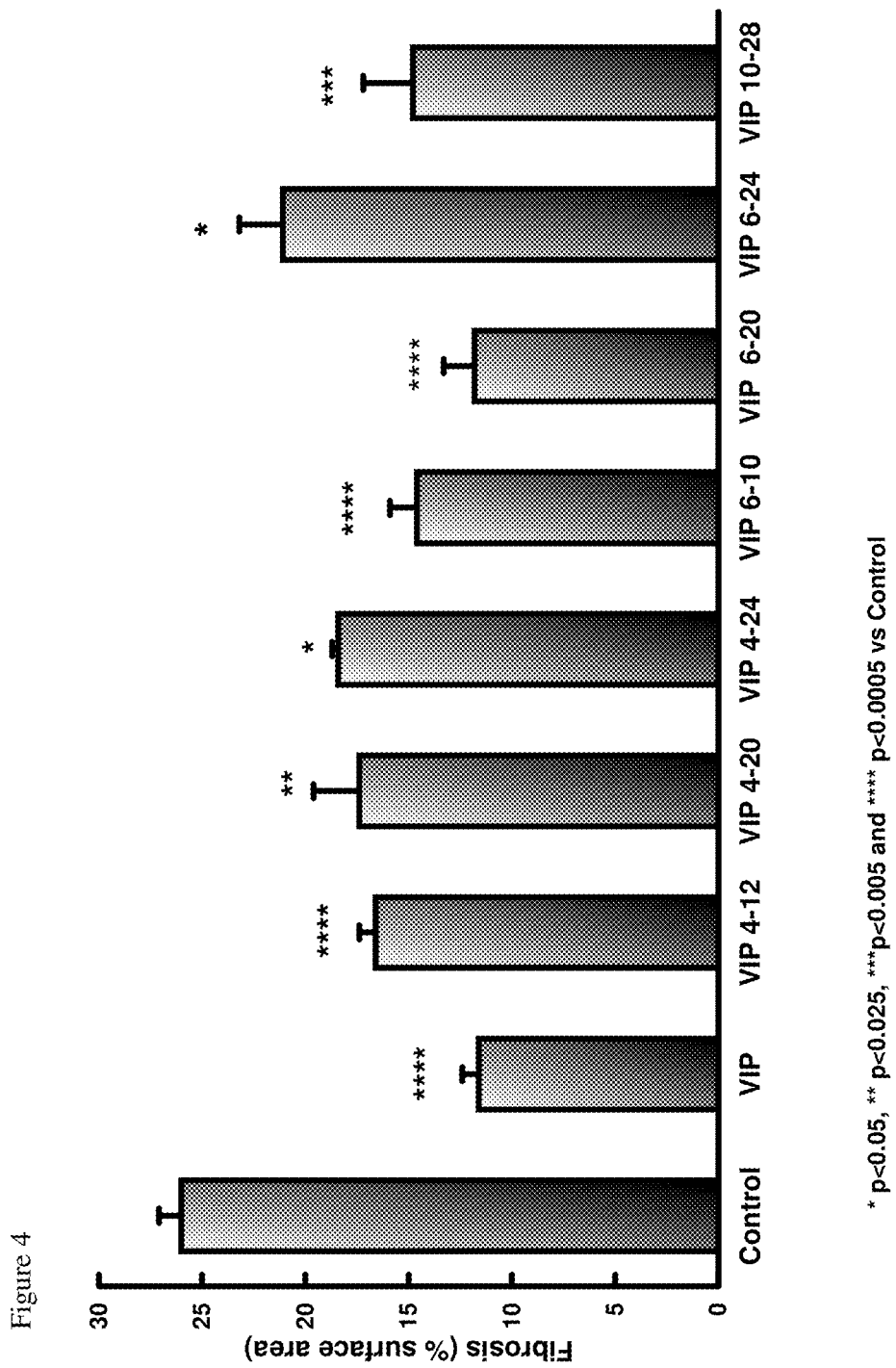
FIG. 4: Renal interstitial fibrosis after infusion of vehicle control or peptide at 5 pmol/kg/min for 4 weeks in the SHR on 2.2% salt diet.

FIGS. 1, 2, 3 and 4, show reductions in renal interstitial fibrosis which occurred as a result of the infusion of VIP and various VIP fragments for 4 weeks in the SHR on a 2.2% salt diet.

In the representative data shown in the figures VB804e refers to VIP(4-12), VB804c refers to VIP(4-20), VB804b refers to VIP(4-24), VB806f refers to VIP(6-10), VB806c refers to VIP(6-20), and VB806b refers to VIP(6-24). Results of studies with VIP fragments not specifically shown in the figures were similar to those for the representative fragments shown.

The importance of the present invention to health care will be immediately apparent to one skilled in the art upon reading this disclosure. Although the capacity to treat chronic kidney disease has improved significantly with the advent of ACE inhibitors, angiotensin receptor blockers and rennin inhibitors, the pharmaceutical preparations of the present invention, which act to prevent the progression of the underlying lesion (fibrosis), or even reverse fibrosis, have the capacity to prevent the escalation of mild to severe disease and hence to substantially reduce the health care burden. The overall size of certain VIP fragments and their activity makes them ideally suitable as targets for drug development.

It is to be appreciated that other embodiments and variants of the compositions, methods and uses of the invention, in keeping with the teaching and the spirit of the invention described, are contemplated and that these are within the scope of the invention.

What is claimed is:

1. A method of therapeutic treatment of kidney fibrosis in a subject, the method comprising administering to a subject having kidney fibrosis a composition comprising a pharmaceutically effective amount of one or more functional vasoactive intestinal peptide (VIP) fragments selected from VIP (10-28), VIP(6-10), VIP(6-12), VIP(6-16), VIP(6-20) and VIP(6-24), optionally in combination with a pharmaceutically acceptable carrier.

2. The method according to claim 1, wherein the kidney fibrosis is associated with chronic kidney disease or kidney failure.

3. The method according to claim 1, wherein the treatment slows down or reduces the degree or intensity of kidney fibrosis.

4. The method according to claim 1, further comprising the simultaneous or sequential administration of one or more other agents active in the treatment of kidney fibrosis, chronic kidney disease or kidney failure.

5. The method according to claim 1 wherein the administration is by oral, intravenous, intramuscular or subcuticular route.

6. A method of reducing the levels of pro-fibrotic mediators, inhibiting or reducing the production of pro-fibrotic mediators, reducing collagen formation or enhancing collagen degradation in a subject having kidney fibrosis, the method comprising administering to a subject having kidney fibrosis a composition comprising a pharmaceutically effective amount of one or more functional VIP fragments selected from VIP(10-28), VIP(6-10), VIP(6-12), VIP(6-16), VIP(6-20) and VIP(6-24), optionally in combination with a pharmaceutically acceptable carrier, thereby reducing the levels of pro-fibrotic mediators, inhibiting or reducing the production of pro-fibrotic mediators, reducing collagen formation or enhancing collagen degradation in the subject having kidney fibrosis.

7. The method according to claim 6, further comprising the simultaneous or sequential administration of one or more other agents active in the treatment of kidney fibrosis, chronic kidney disease or kidney failure.

8. The method according to claim 6 wherein the administration is by oral, intravenous, intramuscular or subcuticular route.

\* \* \* \* \*